United States Patent [19]

Dattagupta et al.

[11] Patent Number: 4,808,520
[45] Date of Patent: Feb. 28, 1989

[54] LABELLING OF OLIGONUCLEOTIDES

[75] Inventors: Nanibhushan Dattagupta, New Haven; William J. Knowles, Hamden, both of Conn.

[73] Assignee: Molecular Diagnostics, Inc., West Haven, Conn.

[21] Appl. No.: 712,481

[22] Filed: Mar. 15, 1985

[51] Int. Cl.$^4$ .................. C12Q 1/68; C12P 19/34
[52] U.S. Cl. ......................................... 435/6; 935/78; 935/8; 435/91
[58] Field of Search ............... 435/6, 803, 91; 436/501, 161; 935/78, 8; 536/27

[56] References Cited

FOREIGN PATENT DOCUMENTS 0184056 6/1986 European Pat. Off. .
0200362 12/1986 European Pat. Off. .

OTHER PUBLICATIONS

Tener, G. M. et al., *Biochemistry*, vol. 17, No. 4, 1978, pp. 741-745.
Dattagupta, N. et al., *Biotechniques*, vol. 5, No. 1, 1987, pp. 38, 39, 42, 43.
Meinkoth, J. et al., *Anal Biochem.*, vol. 138, No. 2, 1984, pp. 267-269.
Kennell, D., In Progress in Nucleic Acid Research and Molecular Biology (Davidson, J. N. et al-ed), vol. 11, 1971, Academic Press, N.Y., pp. 259-261.
Studencki, A. et al., *DNA*, vol. 3, Feb. 1984, pp. 7-15.
*Chem. Abs.*, vol. 101, No. 15, Oct. 8, 1984, p. 69, abst. no. 123160p, Svoboda, M. et al., "One-Step Isocratic... Cholecystokinin".
Randerath, K., *Anal. Biochem*, vol. 115, 1981, pp. 391-397.
Gene, vol. 33, 1985, pp. 191-196, Elseyier Science Publishers, New York, U.S.; K. M. Lang et al.: "Cloning Specific Complete Polyadenylylated 3'-Terminal cDNA Segments".

*Primary Examiner*—Charles F. Warren
*Assistant Examiner*—Jeremy M. Jay
*Attorney, Agent, or Firm*—Sprung Horn Kramer & Woods

[57] ABSTRACT

A method is provided of making an oligonucleotide which comprises hybridizing (a) a shorter fragment of the desired oligonucleotide with (b) a nucleic acid fragment longer than (a) and complementary to the desired oligonucleotide, one of (a) and (b) is linked to an organic radical which differentiates its physical properties relative to the other of (a) and (b), contacting the hybridized material with an enzyme and nucleoside triphosphates whereby the shorter fragment is extended in one direction until it is substantially coterminal with the complementary nucleic acid fragment, denaturing the hybridized material and separating lengthened (a) from (b).

7 Claims, No Drawings

LABELLING OF OLIGONUCLEOTIDES

The present invention relates to methods of making an oligonucleotide. The present invention also concerns methods of making oligonucleotide probes.

It has been shown by Studencki and Wallace (DNA 3, 7 (1984)) that an oligonucleotide can be labeled with radioactive $^{32}P$ using an enzyme and a combination of primer and template. The method is efficient and can produce highly labeled probe. The method has a serious disadvantage because the template and the products have identical electrophoretic mobility unless one is phosphorylated at the 5' end, or the template or the primer is tritylated at one end. This requires that one of the strands be labeled with $^{32}P$ using terminal labeling enzyme, or tritylated and 100% of these molecules should carry the modification.

The modification by phosphorylation is not efficient enough to produce 100% 5' end phosphorylated nucleic acids. Moreover, depending on the sequence, the mobility difference between phosphorylated template extended primer and the other strand may not be enough to separate them. 5'-end tritylated residues have the disadvantage of liability in aqueous solutins. The present invention is a method of separation of primer extended oligonucleotide probes from the templates by modification of one of the participating oligonucleotides. The modification is such that it is stable, hydrophobic/hydrophilic and changes the electrophoretic mobility and elution property on a reverse phase column and if desired reusable. It is desirable that the template be modified to carry the separability property. The synthesized labeled moleculesshould remain unmodified other than the modifications introduced by an enzyme reaction used in the synthesis.

As for example, if the template is modified at the 3' end with hexylamino ATP, the mobility of the template during gel electrophoresis will be slower than the synthesized labeled product. Similar modifications will also give rise to separability during chromatography under high pressure on a reverse phase system. The invention can be further described as follows:

Method 1

3' ──────── 5'
oligonucleotide template
↓ modification with X

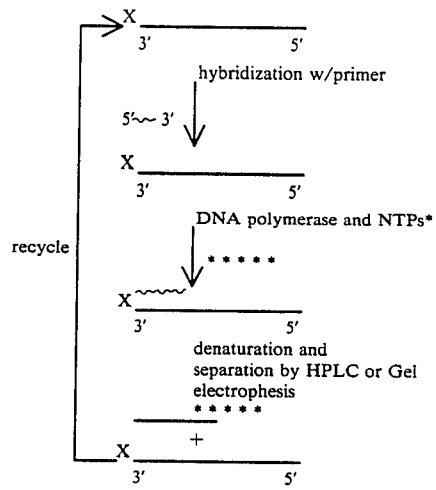

-continued
Method 1

Instead of modifying the template, if a modified nucleoside triphosphate is used, a labeled strand can also be separated.

A different kind of extension reaction can be used to label or synthesize a specific nucleic acid sequence. In Method 1 the template contains the complete sequence of the nucleic acid to be copied (described in the diagram) on the template. A template primer pair can be chosen such that one can be extended to complete a desired sequence without extending the other of the pair. As for example, the following four pairs will produce nonadecanucleotide without the use of one of the same length as the template:

```
19A' ( 5' GCAGACTTCTCCTC           3'
Pair ( 3'          GAAGAGGAGTCCTC  5'
``` and

```
19S' ( 5' GCAGACTTCTCCAC           3'
Pair ( 3'          GAAGAGGTGTCCTC  5'
```

Only the upper strand will be extended if dATP and dGTP are used as NTP substrates for DNA polymerase or reverse transcriptase reaction. This will produce 19A'/S' sequence and unextended lower strand.

Similar complementary strands can be synthesized or labeled by using pyrimidine nucleoside triphosphates instead of dATP and dGTP to produce complementary sequences. The pairs to be used are

```
19S  ( 5' CTCCTGTGGAGAAGTC          3'
Pair ( 3'           CCTCCTCAGACG    5'
```

```
19A  ( 5' CTCCTGAGGAGGAG            3'
Pair ( 3'           CTCCTCTTCAGACG  5'
```

Labeling by using these kinds of pairs is limited to proper sequence selection. Once they are selected using limited required type and amount of nucleoside triphosphates one should be able to prepare larger labeled sequence than the starting reaction partners and hence easy separation from the reactants. Under certain conditions this separation may not be necessary for the hybridization assay.

Using nucleoside triphosphates which are to be added to the desired strand, it is possible to separate the starting materials (unreacted) by gel electrophoresis or by column chromatography.

In order to maintain the fidelity of the process it is desirable that the modification of the template be done at the 3' or 5' end. If a primer is modified its 5' end is the desirable site of alteration. The modification is carried out via

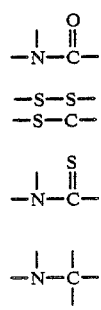

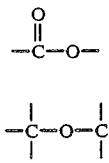

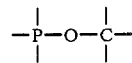

linkages using known reactions and modified nucleic acid residues at the specific site. The modifier can be ionic, nonionic, hydrophobic or hydrophilic. The modification can be before or after the labeling reactions. If the modification is carried out after the labeling reagent should be reactive enough to efficiently modify all the desired residues.

As for example, an oligonucleotide with an amine residue (as in 8-hexylamino A or 5-allylamino U containing oligonucleotide) can be reacted with

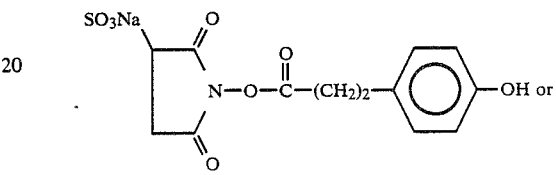

similar reagents to form

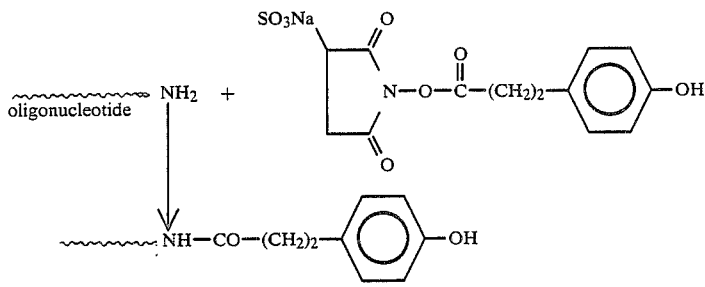

an oligonucleotide with hydrophobic

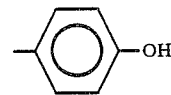

residue. A few other typical reactions are described below.

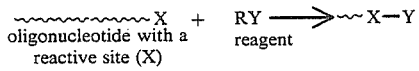

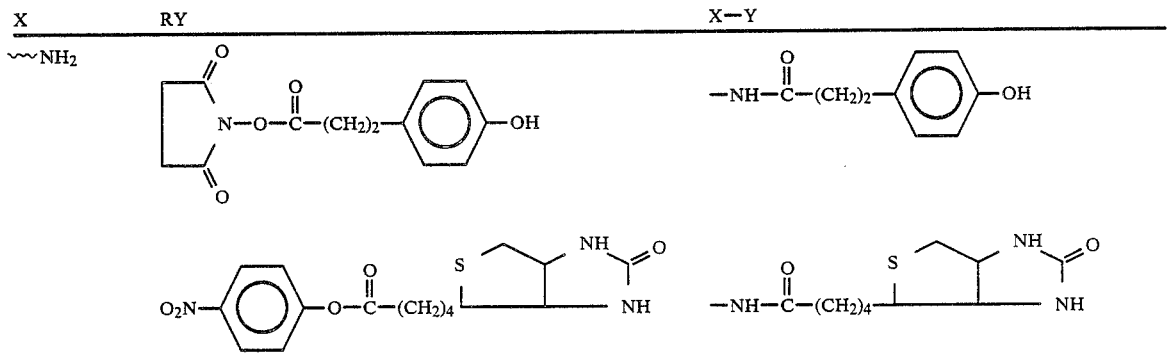

-continued

| X | RY | X—Y |
|---|---|---|
| ~NH₂ | isothiocyanate or isocyanate | ~NH–C(=S)–NH– |
| | Epoxide | ~NH–CH₂–CH(OH)– |
| SH | 2,4 dinitrochlorobenzene | ~S–(2,4-dinitrophenyl) |
| | Iodoacetamide | ~S–CH₂–CONH₂ |
| | Dansylhydrazine | ~S–CH₂–CH₂–NH–dansyl |
| | SH–containing reagent | ~S–S–Reagent |
| ~COOH | Alcohol | Ester |
| ~OH | Epoxide | ether linkage |
| ~P(=O)(OH)–OH | Catalytic esterification (Y) | ~P(=O)(OH)–OY |

EXAMPLE 1

Synthesis of modified oligonucleotide template and modification with a hydrophobic residue.

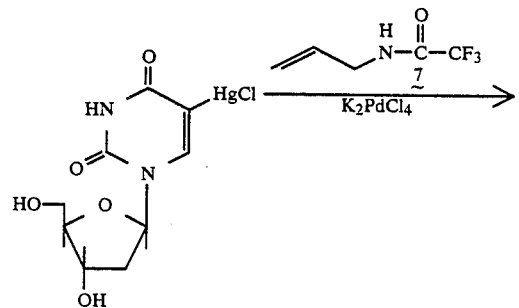

EXAMPLE 1

EXAMPLE 1

-continued

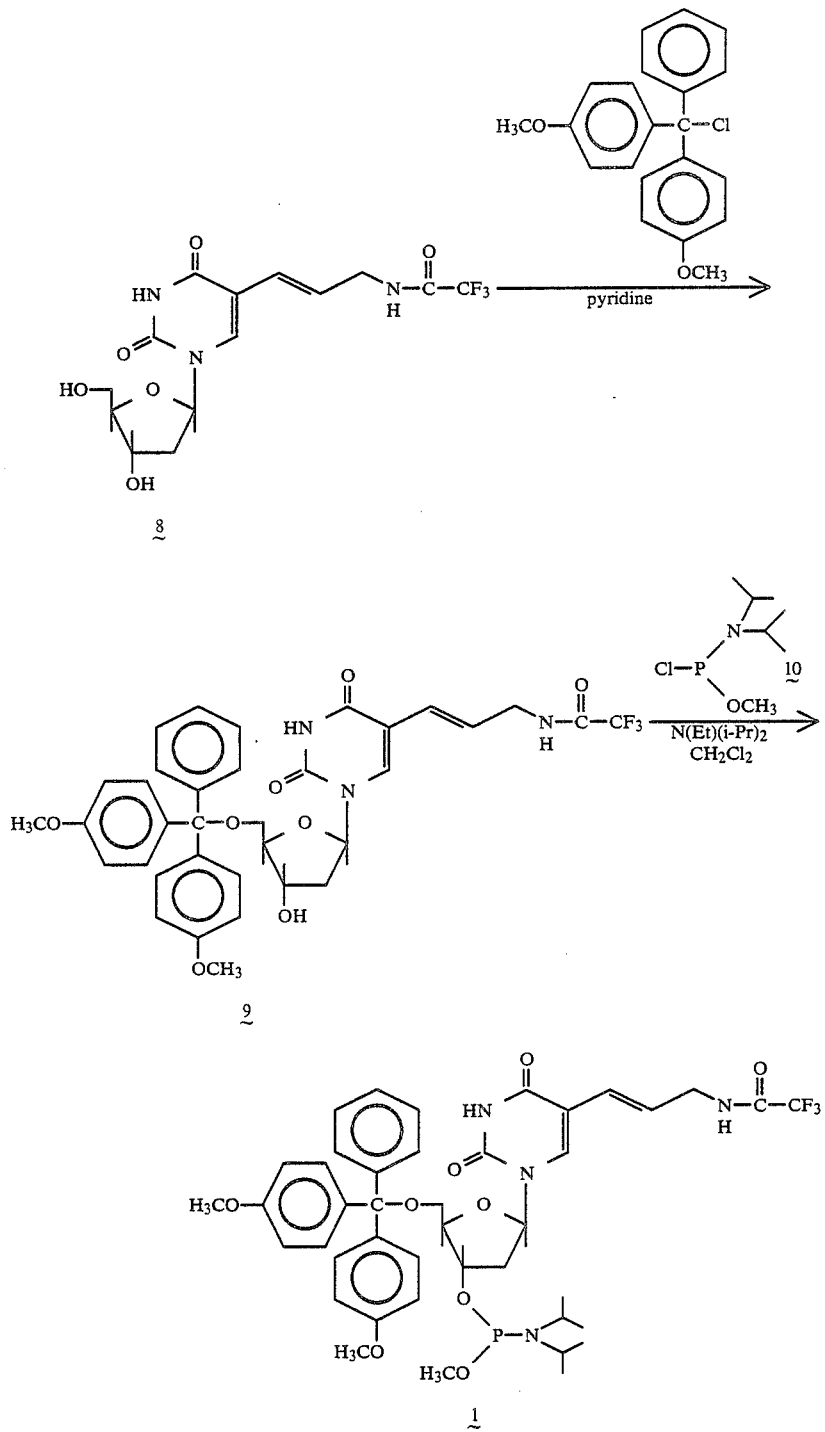

Scheme for the synthesis of 1 to be added to 19A' at the 5' end.

THE SYNTHESIS OF 1 IS OUTLINED IN THE SCHEME

5-Chloromercuri-2'-deoxyuridine (compound 5), prepared according to the method of Bergstrom and Ruth (D. E. Bergstrom and J. L. Ruth, *J. Carbohydrates, Nucleosides and Nucleotides* 4 (5), 257 (1977)) was treated with 3-trifluoroacetamido-1-propene (compound 7) (M. Pailer and W. J. Hübsch, *Monatshefte fur Chemie* 97 (6), 99 (1966)) and K₂PdCl₄ in methanol to give 5-trifluoroacetamidoallyl-2'-deoxyuridine (compound 8) in 22% yield after 2 chromatographies and a crystallization from methanol. Reaction of compound 8 with 4,4-dimethoxytrityl chloride in pyridine afforded compound 9 in 85% yield after flash chromatography (W. C. Still, M. Kahn and A. Mitra, *J. Org. Chem.* 43, 2923 (1978)), which was subsequently treated with N,N-diisopropylaminomethoxy chlorophosphine (L. J. McBride and M. H. Caruthers, Tet. Letters 24 (3), 243 (1983)) (compound 10) to give compound 1 as a white solid after precipitation from pentane.

A 19-unit oligonucleotide (I) was prepared using a DNA

Hβ19A':
3'-GA-GGA-CTC-CTC-TTC-AGA-CG-5'    (I)

synthesizer; three separate 1 umole batches of each oligonucleotide were made and each was attached to a solid support and fully protected. The dimethoxytrityl protecting group was removed from the 5'-terminus and compound 1 was attached to the 19-unit chain without the DNA synthesizer, but using the same reagents and conditions the machine typically employs.

The result of this process is an oligonucleotide with a 5'-aminoallyl-5'-(4,4'-dimethoxytrityl)-2'-deoxyuridine unit at the C-5' end (II).

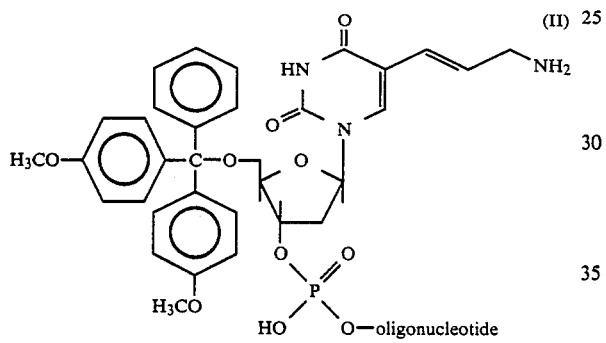

When portions of each of the modified oligonucleotides were treated with 3% trichloroacetic acid in methylene chloride, the distinctive red-orange color of liberated dimethoxytrityl cation was observed, indicating that the 5-allylamino-2'-deoxyuridine moiety had been attached. The polynucleotide were lastly de-tritylated with brief exposure to 3% trichloroacetic acid then purified by polyacrylamide gel electrophoresis. This demonstrates the utility of compound 1 as a synthon for introducing a 5-aminoallyl-2'-deoxyuridine unit at the C-5' terminus of an oligonucleotide; incorporation of this unit at any position in the oligonucleotide should be possible using the same methodology.

The process of attaching an analogue of a Bolton and Hunter (A. E. Bolton and W. M. Hunter, Biochem. J. 133, 529 (1973)) reagent is described in Scheme 2. Reaction of the amino-functionalized polynucleotide compound 11 with the N-hydroxysuccinimide ester of 3-(4'-hydroxyphenyl) propionic acid (compound 12) will yield the probe polynucleotide compound 13.

The polynucleotide Hβ19A' is 19 unit polynucleotides corresponding to a portion of human DNA which codes for the polypeptide hemoglobin, specifically that region of the DNA wherein lies the mutation which manifests itself in the formation of sickle-cell hemoglobin and the genetic disorder known as sickle cell anemia.

Scheme 2

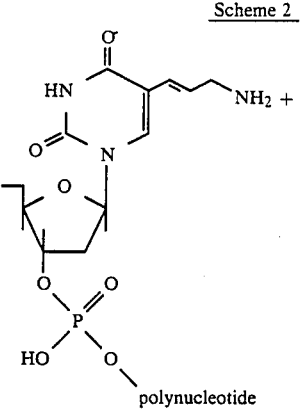

11

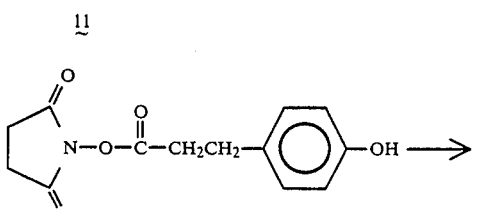

12

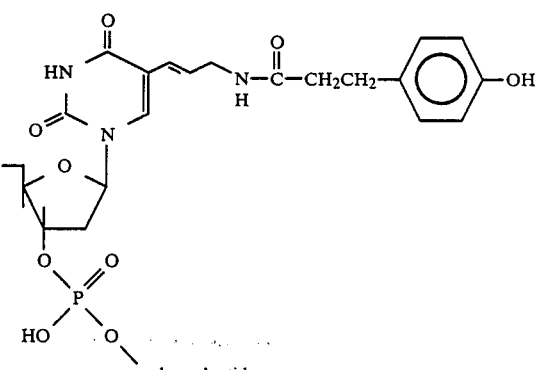

13

EXPERIMENTAL

In the following experimental abbreviations are used as indicated:
g=gram
HPLC=high performance liquid chromatography
L=liter
mL=milliliter
M=molar
mM=millimolar
N=normal
eq=equivalents
mol=gram molecular formula (moles)
mmol=gram molecular formula $\times 10^{-3}$ (millimoles)
aq=aqueous
hr=hour Infrared (IR) spectra were obtained with a Perkin-Elmer Model 710B or 237 infrared spectrophotometer as solutions in $CHCl_3$ unless otherwise noted; the 1602 $cm^{-1}$ band of polystyrene film was used as an external calibration standard. Signals are reported as $cm^{-1}$.

Proton magnetic resonance ($^1$H NMR) spectra were obtained at 89.55 MHz using a Varian T-60 spectrometer; spectra were obtained in CDCl$_3$ solution unless otherwise noted. Chemical shifts are reported in parts per million downfield from the internal standard tetramethylsilane, unless otherwise noted.

Carbon-13 magnetic resonance ($^{13}$C NMR) spectra were obtained at 22.5 MHz using a JEOL FX90Q spectrometer with Fourier transform and with full proton broad-band noise decoupling; spectra were obtained in CDCl$_3$ solution unless otherwise noted. Carbon shifts are reported in parts per million downfield from the internal standard tetramethylsilane, unless otherwise noted.

Phosphorus-31 magnetic resonance ($^{31}$PNMR) spectra were obtained at 36.21 MHz using a JEOL FX90Q spectrometer; spectra were obtained in CDCl$_3$ solution unless otherwise noted. Phosphorus shifts are reported in parts per million downfield from an external aqueous 15% H$_3$PO$_4$ standard.

Optical rotations were obtained on a Perkin-Elmer Model 141 Polarimeter.

Organic reagents were obtained from Aldrich Chemical Company and were used without purification, unless otherwise noted. Inorganic reagents were ACS reagent grade from Fisher Scientific Company or other major vendor. Reaction solvents were ACS reagent grade. Reagents used in oligonucleotide synythesis were obtained from Applied Biosystems, Inc. Brine refers to a saturated aqueous sodium chloride solution.

Thin layer chromatography (TLC) was performed using silica gel 60F-254 plates from E. Merck. Column chromatography was performed using E. Merck Silica Gel 60 (70–230 mesh). All melting points reported are uncorrected.

5-TRIFLUOROACETAMIDOALLYL-2'-DEOXYURIDINE (COMPOUND 8)

A suspension of 5-chloromercuri-2'-deoxyuridine (compound 5) (D. E. Bergstrom and J. L. Ruth, *J. Carbohydrates, Nucleosides and Nucleotides* 4 (5), 257 (1977)) (5.56 g; 12 mmol) in HPLC grade methanol (120 ml) was maintained under an inert gas atmosphere at ambient temperature and treated with 3-trifluoroacetamido-1-propene (compound 7) (M. Pailer and W. J. Hübsch, *Monatschefte fur Chemie,* 97 (6), 99 (1966)) (7.33 g; 48 mmol; 4 eq) and K$_2$PdCl$_4$ (4.28 g; 1.1 eq). The reaction gradually became black and was allowed to stir for 22 hr. The mixture was treated with H$_2$S gas for several minutes then filtered through Celite, rinsed with MeOH and evaporated to dryness under reduced pressure from a 80° C. bath to give a crude semi-solid residue (7.0 g). The residue was chromatographed on a silica gel column developed with CH$_2$Cl$_2$/MeOH (5:1). The band which stained a blue color with modified p-anisaldehyde reagent (*Thin Layer Chromatography* by Egon Stahl, 2nd ed. Springer-Verlag, New York 1969, page 857) and had an Rf=0.51 (CH$_3$CN/MeOH 3:1) was collected and evaporated to dryness in vacuo to give a colorless foam. The product was crystallized from a minimum of methanol, filtered, washed with cold CHCl$_3$/MeOH (3:1) and vacuum dried. The mother liquor was worked for a second crop-total yield 1.01 g (22%). A recrystallization from MeOH afforded the title compound (8) as analytically pure tiny white needles with mp=183°–4° C. after drying in vacuo (<1.0 torr) at 64° C. overnight. IR (KBr) cm$^{-1}$ 3420, 3260, 1718, 1683 (br), 1560, 1478, 1283, 1190, 1102, 1061, 980, 788, 763, 737; $^1$HNMR (DMSO-d$^6$) (Ref.-DMSO-d$^6$) δ 2.13 (d of d, J=6 Hz, 2H), 3.59 (br s, 2H), 3.70–3.97 (m, 3H), 4.25 (br s, 1H), 5.06 (br m, 1H), 5.20 (br m, 1H), 6.05–6.65 (m 4H), 8.01 (s, 1H), 9.60 (br s 1H); $^{13}$C NMR (DMSO-d$^6$) (Ref. DMSO-d$^6$) ppm 162.05, 155.29, 149.50, 138.05, 124.33, 124.14, 109.96, 87.53, 84.47, 70.23, 61.12, 39.93; [α]$_D$= +8.01° (c=0.87, MeOH).

Anal. Calcd. for C$_{14}$H$_{16}$N$_3$O$_6$F$_3$: C, 44.33; H, 4.25; N, 11.08. Found: C, 44.19; H, 4.10; N, 10.93.

5-TRIFLUOROACETAMIDOALLYL-5'-O-(4,4'-DIMETHOXYTRITYL)-2'-DEOXYURIDINE (COMPOUND 9)

A solution of compound 8 (0.60 g; 1.58 mmol) in anhydrous pyridine (8 ml) was maintained under an inert gas atmosphere and treated at ambient temperature with 4,4'-dimethoxytrityl chloride (0.67 g; 1.25 eq). After stirring for 18 hr the reaction was poured into ice water (70 ml) with vigorous shaking. On standing ⅓ hr at 0° a gummy solid separates leaving a nearly clear solution which was decanted. The solid was washed once with H$_2$O (5 ml) then taken up in CH$_2$Cl$_2$ (10 ml), washed once with brine (5 ml) then the CH$_2$Cl$_2$ solution was dried over K$_2$CO$_3$, filtered and evaporated to dryness in vacuo to give a brownish foam. The crude product was purified by flash chromatography (W. C. Still, M. Kahn and A. Mitra, *J. Org. Chem.* 43, 2923 (1978)) on a column of silica gel (Merck, Grade 60, 230–400 mesh, 60 A) (75 g) developed with 4.0% MeOH in CHCl$_3$ solvent (1.0 L). Fractions of ca. 20 ml each were collected in tubes containing pyridine (10 μl) to inhibit deprotection of the 5'-hydroxyl. Fractions containing the major product band (RF=0.29; MeOH/CHCl$_3$ 7:93) were combined, filtered and evaporated to dryness in vacuo to give compound 9 (0.91 g; 85%) as a slightly yellowish foam. A fraction from the center of the elution band was freed of solvent, taken up in EtOAc, treated with Norit 211, filtered through Celite and evaporated to dryness under high vacuum (<1.0 torr) at 64° C. overnight to afford the analytical sample as a colorless foam with mp=105°–110° C. (dec.). IR (CHCl$_3$) cm$^{-1}$ 3370, 2920, 1715, 1695, 1618, 1515, 1470, 1260, 1182, 1045, 842; $^1$H NMR (CDCl$_3$) δ 2.38 (br m, 2H), 3.25–3.75 (m, 5H), 3.75 (s, 6H), 4.10 (br m 1H), 4.60 (br s, 1H), 5.39 (d, J=16 Hz, 1H), 6.10–6.55 (m, 2H), 6.70–6.95 (m, 5H), 7.15–7.45 (m, 10H), 7.84 (s, 1H); $^{13}$C NMR (CDCl$_3$) (Ref. CDCl$_3$) ppm 162.31, 158.74, 157.70, 156.01, 149.70, 144.04, 137.88, 135.65, 135.52, 130.12, 128.11, 127.26, 125.05, 113.48, 111.33, 86.94, 86.68, 85.25, 72.18, 63.60, 55.34, 42.66, 41.42.

Anal. Calcd. for C$_{35}$H$_{34}$N$_3$O$_8$F$_3$: C, 61.67; H, 5.03; N, 6.16. Found: C, 61.47; H, 5.19; N, 5.95.

5-TRIFLUOROACETAMIDOAMINOALLYL-5'-O-(4,4'-DIMETHOXYTRITYL)-2'-DEOXYURIDINE-3'-O-(N,N-DIISOPROPYLAMINOMETHOXY PHOSPHINE (COMPOUND 1)

A solution of compound 9 (0.34 g; 0.5 mmol) in anhydrous CH$_2$Cl$_2$ (1.5 ml) maintained under an Argon atmosphere at ambient temperature was treated first with anhydrous diisopropylethylamine (0.35 ml; 0.259 g; 2 mmol; 4 eq) then dropwise, over 1 minute, with N,N-diisopropylaminomethoxychlorophosphine (L. J. McBride and M. H. Caruthers, *Tet. Letters* 24 (3), 245 (1983)) (compound 10) (0.19 ml; ca. 0.2 g; 2.2 eq). The resultant colorless solution is stirred for 20 min then transferred with EtOAc (20 ml) (EtOAc was previously washed with saturated aq NaHCO$_3$ then brine) to a separatory funnel, washed four times with brine (35 ml each), dried over N$_2$SO$_4$, filtered and evaporated to dryness in vacuo to give a colorless glass (0.51 g). This crude product was taken up in anhydrous benzene (2 ml) and precipitated into rapidly stirred anhydrous pentane (60 ml) at $-78°$ C. under an Argon atmosphere. The resulting suspension was filtered, washed with $-78°$ C. pentane and vacuum dried at <1 torr over KOH overnight to obtain the title compound 1 (0.38 g; 93%) as a white amorphous powder. IR (CHCl$_3$) cm$^{-1}$ 2965, 1722, 1698, 1618, 1518, 1470, 1262, 1185, 1045, 988, 842; 'H NMR (CD$_2$Cl$_2$) δ 0.95–1.30 (m, 12H), 2.20–2.60 (m, 2H), 3.24 and 3.37 (d of d, J=13 hz, 3H) (P-O-CH$_3$), 3.20–3.80 (m, 6H), 3.75 (s, 6H), 4.17 (br m, 1H), 4.68 (v br m, 1H), 5,42 (d, J=16 Hz, 1H), 6.15–6.55 (m, 3H), 6.75–6.95 (m, 4H), 7.20–7.50 (m, 10H), 7.79 (s, 1H); $^{13}$C NMR (CD$_2$Cl$_2$) (Ref. CD$_2$Cl$_2$) ppm 162.40, 159.21, 157.78, 149.78, 144.71, 138.34, 136.00, 130.53, 128.71, 128.45, 127.54, 125.66, 125.27, 113.82, 111.48, 87.23, 86.31, 85.60, 55.75, 43.78, 43.20, 42.94, 24.99, 24.60; $^{31}$PNMR (CD$_2$Cl$_2$) ppm 149.30, 148.87, 14.11 (ca. 12% impurity), 8.18 (ca. 4% impurity).

ATTACHMENT OF COMPOUND 1 TO OLIGONUCLEOTIDES

The 19-unit oligonucleotides were synthesized using an Applied Biosystems Model 380A DNA Synthesizer on control pore glass solid support. Immediately prior to attaching compound 1 to the 5' end of the oligomer, the 5'-O-(4,4'-dimethoxytrityl) protecting group was cleaved on the machine with 3% CCl$_3$CO$_2$H in CH$_2$Cl$_2$ for 90 seconds. The support-bound 5'-deprotected oligomer was washed with CH$_3$CN and dried in an Argon stream. Subsequent steps were performed without the machine, but using the same chemistry;

1. The support-bound oligomer was removed from the container (column) used for automated synthesis and transferred to a dry septum-cap vial under an Argon atmosphere.
2. The bound oligomer was treated with a 20–30 fold excess of 0.5M 1H-Tetrazole in anhydrous CH$_3$CN followed immediately with a similar excess of compound 1 in Ch$_3$CN. Incubate 30 min with gentle agitation.
3. Pipette off reagents and wash bound oligomer with 3 portions of CH$_3$CN.
4. Treat with an excess of I$_2$-H$_2$O-Lutidine-THF (0.1M: 1:10:40) and agitate for 15 minutes.
5. Pipette off reagent and wash bound oligomer with 4 portions of CH$_3$CN.
6. Treat with an excess of Thiophenol-triethylamine-dioxane for 60 minutes.
7. Pipette off reagent and wash the bound oligomer with 4 portions of MeOH.
8. Treat with conc. aq. NH$_4$OH for 2 hr at ambient temperature. (Removes protected oligonucleotide from the support).
9. Add more conc. aq. NH$_4$OH and heat at 50° C. overnight. (Removes all protecting groups except the dimethoxytrityl)
10. Filter off the support and evaporate the filtrate to dryness to get crude oligonucleotide.

This was repeated for all batches of support-bound oligonucleotide. Treatment of a portion of each on a silica gel TLC plate with 3% CCl$_3$CO$_2$H in CH$_2$Cl$_2$ produced the orange-red color of dimethoxytrityl cation indicating the successful incorporation of compound 1 into the oligonucleotides.

One bath of the modified Hβ19A' oligonucleotide was detrytylated with 3% CCl$_3$CO$_2$H in CH$_2$Cl$_2$ then purified by electrophoresis on a 20% polyacrylamide gel under denaturing conditions.

EXAMPLE 2

The reaction of a specific oligonucleotide with sulfosuccinimidyl hydroxy phenyl propionate.

Two micrograms of 19A' amine product of Example 1 is dissolved in 20 microliter of 10 mM borate buffer pH 8.16. To this 5 microliter of a freshly prepared solution of sulfosuccinimidyl 3-(4-hydroxyphenyl) propionate (SHPP) purchased from Pierce is added. Concentration of SHPP is 5 mg per ml in water. The reaction is allowed to proceed at room temperature for 30 minutes then it is kept in the freezer before HPLC separation is done.

After the reaction, the extent of the reaction is monitored by running a 20% polcrylamide gel in conventional manner.

EXAMPLE 3

Separation of the SHPP reacted 19A' from the reaction mixture containing hydrolyzed SHPP and oligonucleotides.

HPLC run has been done on a Brownlee RP300 guard column coupled to a Synchrome RP-P 4.1×10 cm column at ambient temperature. A gradient of (a) 0.1M triethylammonium acetate pH 7 with (b) 0.1M triethylammonium acetate pH 7.0, 50% acetonitrile at a flow rate of 1 ml/minute. The uv detector at 254 mm is used to monitor the elution of oligonucleotide. In order to find out the location of the product, a blank run has been done with all of the reactants in the starting mixture without the oligonucleotide. The new peak appeared after adding the oligonucleotide is taken to be the peak corresponding to the reaction product. After the product is separated and collected in a fraction collector, the product is analyzed by gel electrophoresis and from the next run an analytical determination of the proper peak is not necessary. The yield and recovery of the product from the columns is between 80% to 90%.

EXAMPLE 4

Primer extension reaction for labeling an oligonucleotide.

The product of Examples 1 or 3 can be used as template and both are separable by HPLC (high pressure liquid chromatography) or gel/electrophoresis. An example is provided with the product of Example 1. An identical procedure can be followed with the product of Example 3.

Reaction conditions have been discussed by Studencki and Wallace, DNA 3 (1984) 7. Primer extension reaction mixture contained 25 μl total volume and is prepared by mixing to produce a final concentration of 1.6 μM template (3' GAGGACTCCTCTTCAGACG U*-5') (U* is 5-allylamino U)

and 5.0 μM primer (5' CTCCTGAGGAG-3')

and 5 μM each of dATPO, dTTP, alpha-[32P] dCTP and alpha-[32P] dGTP, and 10 units of *E. coli* DNA polymerase I (Klenow fragment) purchased from New England Nuclear. The reaction is allowed to proceed for 18 hours at room temperature.

EXAMPLE 5

Purification of the product by gel electrophoresis.

When the product of Example 1 or 3 is used as templates, the electrophoretic mobility (on a 20% polyacrylamide gel) of the product is different than the template and the short primer. The reaction mixture (Example 4) is diluted to 40 μl with loading buffer containing 8M urea, 0.05% xylene cyanol FF and 0.05 Bromophenol blue in 20 mM tris EDTA buffer (pH 7.5). The mixture 40 μl is loaded onto a 20% polyacrylamide slab gel (0.2×15.5×29.5 cm) which has been preelectrophoresed for 1 hour at 1000 V. The gel is run for 8 hours at 1000 V in 50 mM trisborate buffer pH 8.3. After the run autoradiographic detection is done to locate the radioactive product band; it is excised and eluted from the gel using 1 mM EDTA solution as described by Studencki and Wallace (DNA, 3 (1984)7).

EXAMPLE 6

Purification of the product by high pressure liquid chromatography.

Both the products of Examples 1 and 3 are more hydrophobic than their parent oligonucleotide. They can be separated from the labeled complementary stand on a reverse phase system using acetonitrile gradient. An identical device and reaction conditions as have been described in Example 3 are used to separate the labeled product from the template. In this method a part of the primer (unreacted) coelutes with the product. This can be purified on a gel filtration system.

EXAMPLE 7

Hybridization of the product of Example 5 or 6 with DNA from β-globin gene.

The specific oligonucleotide fragment chosen for the examples (5,6) is usable for the detection of sickle cell anemia. This particular sequence of oligonucleotide will hybridize with DNA extracted from normal blood and under certain conditions it will not hybridize to the DNA extracted from the blood of a person who has sickle cell anemia disease. The extraction of DNA from blood samples and the digestion with a restriction enzyme and other appropriate treatment of the hybridization process have been described by Studencki and Wallace (DNA 3 (1984) 7)). The newly labeled material shows similar hybridization property as a $^{32}P$ labeled probe as has been described by Studencki & Wallace (DNA 3 (1984) 7)).

It will be understood that the specification and examples are illustrative but not limitative of the present invention and that other embodiments within the spirit and scope of the invention will suggest themselves to those skilled in the art.

What is claimed:

1. A method of making an oligonucleotide probe which consists essentially of hybridizing a template primer pair of oligonucleotides of equal lengths, each of said oligonucleotides of the template primer pair being shorter than the desired probe and being complementary with one another over only a portion of their lengths at opposite ends, contacting the hybridized oligonucleotide pair with an enzyme and one or more nucleoside triphosphates, the one or more nucleoside triphosphates permitting extension of one of the oligonucleotides, whereby one of the oligonucleotides is extended selectively in one direction until it is coterminal with the other oligonucleotide.

2. A method according to claim 1, wherein the nucleoside triphosphates include a label, whereby the extended fragment is linked to said label.

3. A method according to claim 1, wherein the label is radioactive.

4. A method according to claim 1, wherein the fragments comprise

5' GCAGACTTCTCCXC 3'
GAAGAGGYGTCCTC wherein one of X and Y is T and the other is A.

5. A method according to claim 1, wherein the enzyme is DNA polymerase.

6. A method according to claim 1, wherein the enzyme is reverse transcriptase.

7. A method according to claim 1, wherein the hybridized region of the template primer pair is of nine nucleotide residues.

* * * * *